US012636477B2

(12) United States Patent
Shadduck

(10) Patent No.: US 12,636,477 B2
(45) Date of Patent: May 26, 2026

(54) SYSTEMS AND METHODS FOR TREATING SKIN

(71) Applicant: John H. Shadduck, Menlo Park, CA (US)

(72) Inventor: John H. Shadduck, Menlo Park, CA (US)

( * ) Notice: Subject to any disclaimer, the term of this patent is extended or adjusted under 35 U.S.C. 154(b) by 0 days.

(21) Appl. No.: 18/475,015

(22) Filed: Sep. 26, 2023

(65) Prior Publication Data

US 2024/0325704 A1 Oct. 3, 2024

Related U.S. Application Data

(60) Provisional application No. 63/535,896, filed on Aug. 31, 2023, provisional application No. 63/493,948, filed on Apr. 3, 2023.

(51) Int. Cl.
*A61M 37/00* (2006.01)
*A61K 41/00* (2020.01)

(52) U.S. Cl.
CPC ..... *A61M 37/0092* (2013.01); *A61K 41/0023* (2013.01)

(58) Field of Classification Search
CPC .............. A61M 5/3202; A61M 5/3137; A61M 37/0092; A61M 2037/0007; A61K 41/0023
See application file for complete search history.

(56) References Cited

U.S. PATENT DOCUMENTS

| | | | |
|---|---|---|---|
| 6,126,619 A * | 10/2000 | Peterson ............ | A61B 17/2251 601/2 |
| 10,456,321 B2 | 10/2019 | Shadduck | |
| 2002/0055693 A1* | 5/2002 | Thompson ............... | A61N 7/00 601/2 |
| 2008/0319375 A1* | 12/2008 | Hardy ...................... | B82Y 5/00 600/431 |
| 2009/0312693 A1* | 12/2009 | Thapliyal .......... | A61M 37/0092 601/2 |
| 2016/0038183 A1* | 2/2016 | Ignon ..................... | A61B 50/22 606/131 |
| 2017/0056636 A1* | 3/2017 | Shadduck ............ | A61H 9/0057 |
| 2017/0065836 A1* | 3/2017 | Reed .................. | A61M 35/003 |
| 2025/0073439 A1 | 3/2025 | Shadduck | |

OTHER PUBLICATIONS

Matsunaga, T. et al., "Phase-Change Nanoparticles Using Highly Volatile Per-fluorocarbons: Toward a Platform for Extravascular Ultrasound Imaging," *Theranostics*, vol. 2(12), pp. 1185-1198, Dec. 23, 2012.

(Continued)

*Primary Examiner* — Bhisma Mehta
*Assistant Examiner* — Fatimata Sahra Diop
(74) *Attorney, Agent, or Firm* — Levine Bagade Han LLP

(57) ABSTRACT

A skin treatment system that uses ultrasound devices, and more particularly, handheld devices with an ultrasound transducer used in combination with a continuous flow of serum carrying acoustically responsive media wherein acoustic energy transmitted from the transducer causes dimensional changes in the acoustically responsive media to create acoustic pressure peaks capable of loosening para-cellular junctions in the skin to enhance penetration of serum into the skin.

18 Claims, 20 Drawing Sheets

(56)              References Cited

OTHER PUBLICATIONS

Yusefi, H. et al., "Ultrasound Contrast Imaging: Fundamentals and Emerging Technology," *Frontiers in Physics*, vol. 10, pp. 1-16, Feb. 17, 2022.
Zullino, S. et al., "From Micro- to Nano-Multifunctional Theranostic Platform: Effective Ultrasound Imaging Is Not Just a Matter of Scale," *Molecular Imaging*, vol. 17, pp. 1-16, Sep. 13, 2018.

* cited by examiner

FIG. 17A                    FIG. 17B

SYSTEMS AND METHODS FOR TREATING SKIN

RELATED APPLICATIONS

This application is a non-provisional of U.S. Provisional application No. 63/493,948, filed Apr. 3, 2023, and of U.S. Provisional application No. 63/535,896, filed Aug. 31, 2023, the entirety of both of which are incorporated by reference.

BACKGROUND

The present invention relates to skin treatment systems and, more particularly, to a combination system with a first component comprising a device with an ultrasound transducer and a cooperating second component comprising a serum carrying ultrasonically responsive media that can be activated by ultrasound energy for topical treatment of targeted skin for cosmetic or skin rejuvenation purposes.

SUMMARY OF THE INVENTION

The systems and methods corresponding to the invention relate in general to a combination system for use in the fields of skin care, lip care, and hair restoration, wherein the combination includes (i) a handheld applicator with an ultrasound transducer that is coupled to a negative pressure source, (ii) a cooperating skin care treatment serum that carries, or can be infused with, ultrasonically responsive media such as microbubbles wherein the negative pressure source is configured to apply negative pressure to skin in a distal tip of the applicator to provide a continuous flow of serum in a sealed space between the ultrasound transducer and targeted skin. A method corresponding to the invention comprises actuating the transducer to insonate the serum and cause dimensional changes in the acoustically responsive media, which in turn creates acoustic pressure peaks in the sealed space to loosen paracellular junctions in the skin surface, which then enhances penetration of the serum into skin.

In general, a skin care composition or serum corresponding to the invention comprises a dermatologically acceptable carrier that carries or is infused with an effective amount of acoustically responsive media that are adapted to change in dimension or oscillate in response to acoustic energy from an ultrasound transducer at a frequency range of 0.25 MHz to 5 MHz.

The present disclosure includes systems and methods of enhancing the permeability of a targeted skin. In one such variation, a method can include applying acoustic energy to a flow of a serum captured in a sealed space in a distal tip of an applicator wherein when the distal tip is against the targeted skin, the sealed space is defined by (i) an ultrasound transducer in a central portion of the distal tip, (ii) a peripheral sealing portion around a periphery of the distal tip configured to form a seal against the targeted skin and (iii) the targeted skin, wherein applying acoustic energy from the ultrasound transducer causes a dimensional change in an acoustically responsive media in the flow of the serum captured in the sealed space thereby creating acoustic pressure that loosens paracellular junctions in the targeted skin.

Variations of the method can further include introducing the flow of the serum into the sealed space through at least one inflow port inward of the peripheral sealing portion.

The methods can also include applying a negative pressure in the sealed space through an aspiration port inward of the peripheral sealing portion.

Variations of the method can include an acoustic pressure that has peak pressures of at least 0.1 MPa. The methods described herein can apply acoustic energy to create pressures in the range of at least 0.1 MPa, at least 0.5 MPa, or at least 1.0 MPa.

In additional variations, the method comprises a negative pressure that causes the flow of serum into the sealed space from at least one inflow port.

The method can also include introducing a flow of gas into the distal tip to mix with the serum, wherein the gas comprises acoustically responsive media.

In some variations, the distal tip comprises a recessed region of the central portion that is recessed from the peripheral sealing portion. The recessed region can be bounded by one or more spacing elements configured to space apart the surface of the ultrasound transducer and the targeted skin, thereby maintaining a selected dimension of the sealed space for capturing serum.

In an additional variation, the spacing elements can comprise at least one of ridges, bumps, and surfaces distal of the recessed region. Additionally, or alternatively, the recessed region comprises at least one of channels, grooves, dimples, and bores.

In an additional variation, the surface of the ultrasound transducer comprises a matching layer disposed over a piezoelectric crystal where the spacing elements and recessed region are carried in the matching layer.

In any variation of the method, the acoustic energy can be applied from the matching layer having a surface area of at least 1 cm2. Moreover, the acoustic energy can be applied from the matching layer having a surface area ranging from 1 cm2 to 20 cm2.

Another variation of the method can further include moving the distal tip over the targeted skin with the peripheral sealing portion forming a seal against the targeted skin to maintain the sealed space contemporaneous with introducing the serum.

Another variation of a method of applying a serum to a targeted skin surface comprises providing a continuous flow of a serum and a continuous flow of a gas in an interface between an ultrasound transducer and targeted skin, applying acoustic energy from the ultrasound transducer to the continuous flow of serum and gas in the interface and causing a dimensional change in gas mixed in the serum to thereby create an acoustic pressure that loosens paracellular junctions in the targeted skin to enhance penetration of the serum in the targeted skin.

A variation of the methods can include the interface that comprises a sealed space for capturing the continuous flow of serum, wherein the sealed space is defined by (i) a matching layer of the ultrasound transducer, (ii) a peripheral sealing portion around a periphery of the ultrasound transducer configured to form a seal against a targeted skin, and (iii) the targeted skin.

In an additional variation, the ultrasound transducer and peripheral sealing portion comprise a distal tip of a handheld applicator, and the continuous flow of serum flows between an inflow port and an outflow port in the distal tip.

In another variation, the method can include continuous flow of serum between the inflow port and the outflow port that is restricted by at least one flow restriction element between the inflow port and the outflow port in the distal tip.

It will be understood that other objects and purposes of the invention, and variations thereof, will be apparent upon reading the following specification and inspecting the accompanying drawings. These and other features, aspects, and advantages of the present invention will become better understood with reference to the following drawings.

DETAILED DESCRIPTION OF THE INVENTION

Figure 1:
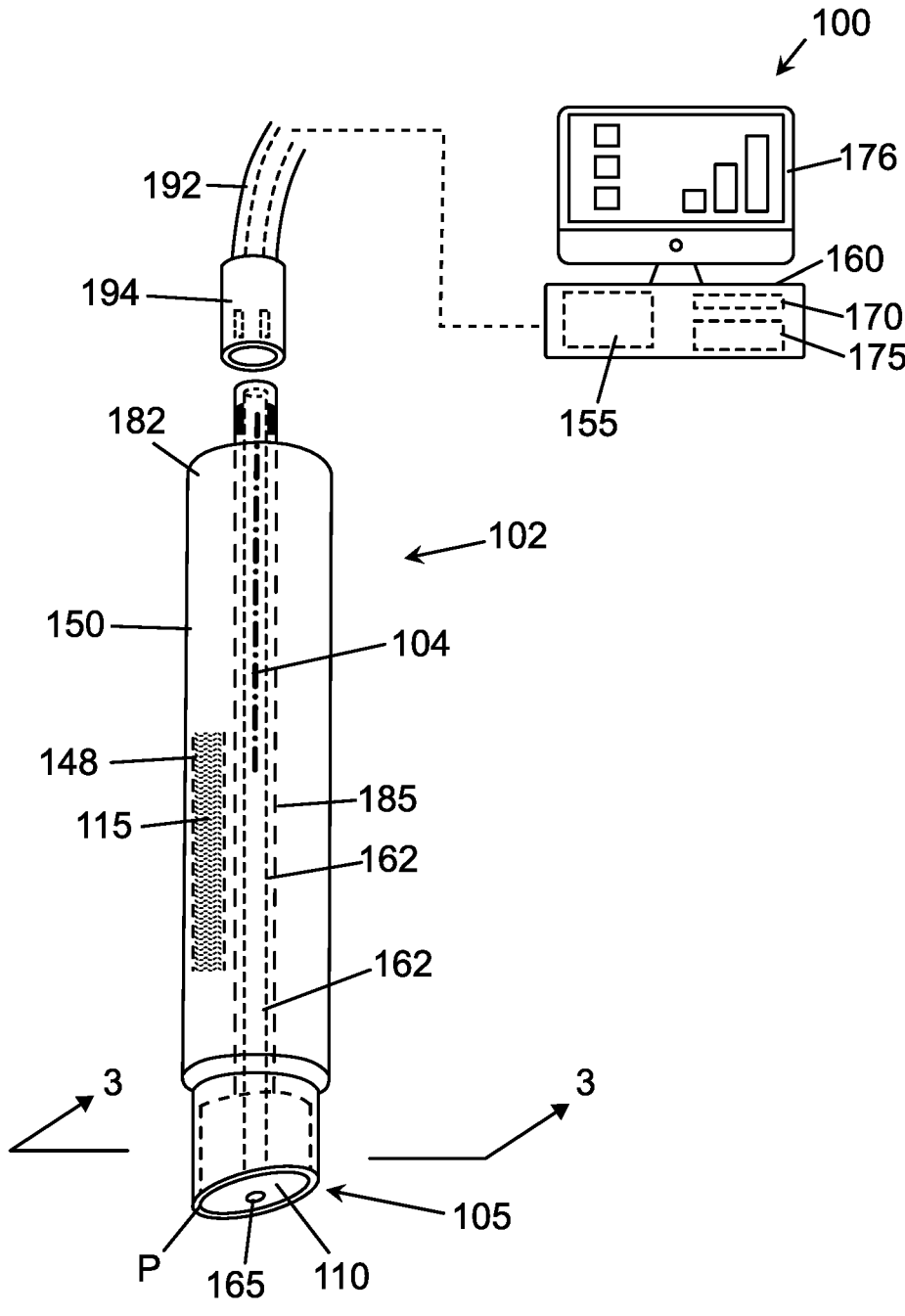
FIG. 1 is a skin treatment system corresponding to the invention adapted for enhancing fluid penetration into a subject's skin, with a handheld applicator carrying an ultrasound transducer and a flowable treatment serum, wherein the ultrasound transducer is adapted for applying acoustic energy to acoustically responsive media in the serum, with the applicator coupled to a console carrying a negative pressure source.
Figure 2:
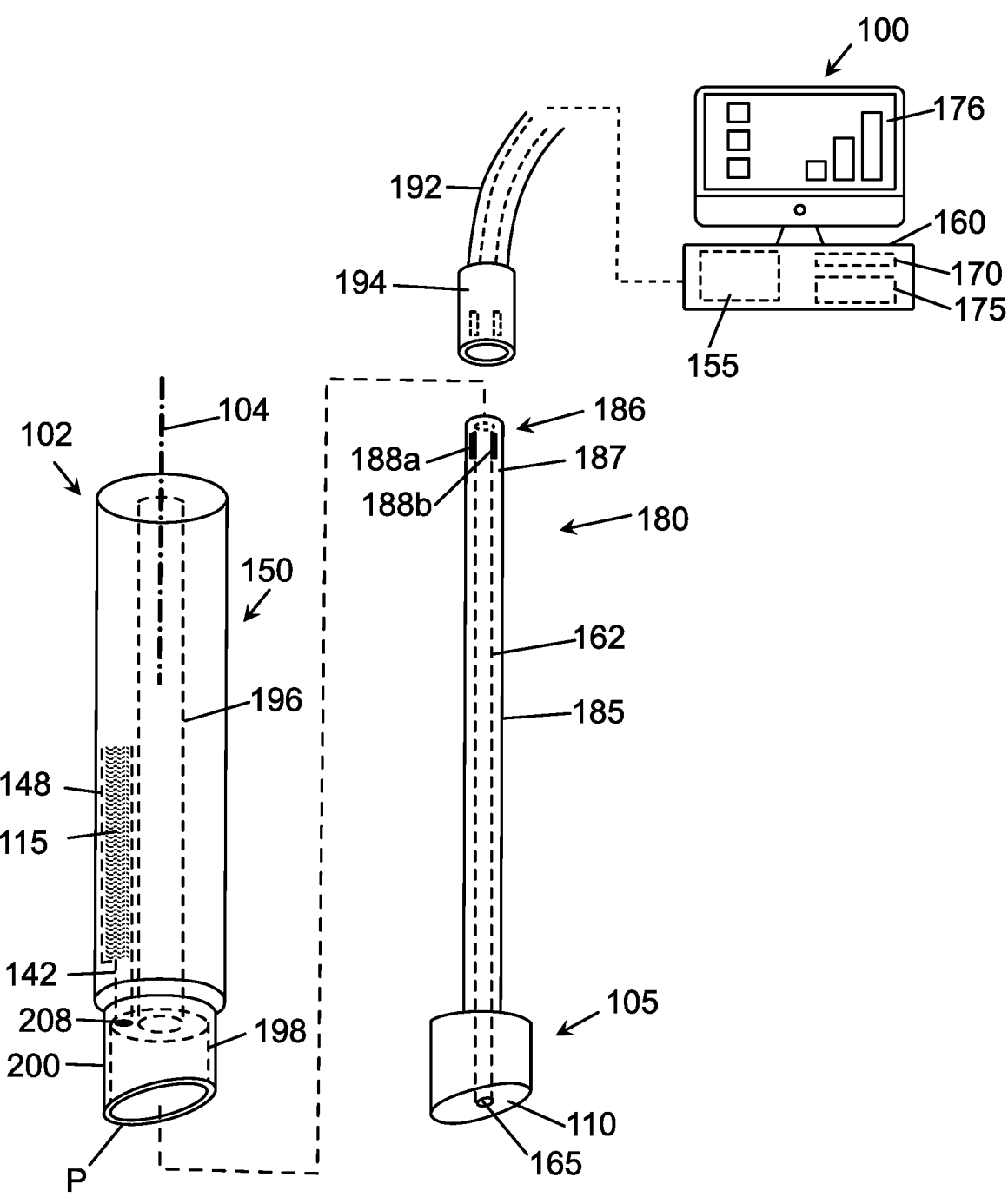
FIG. 2 is another view of the applicator of FIG. 1 with its component parts separated.
Figure 4:
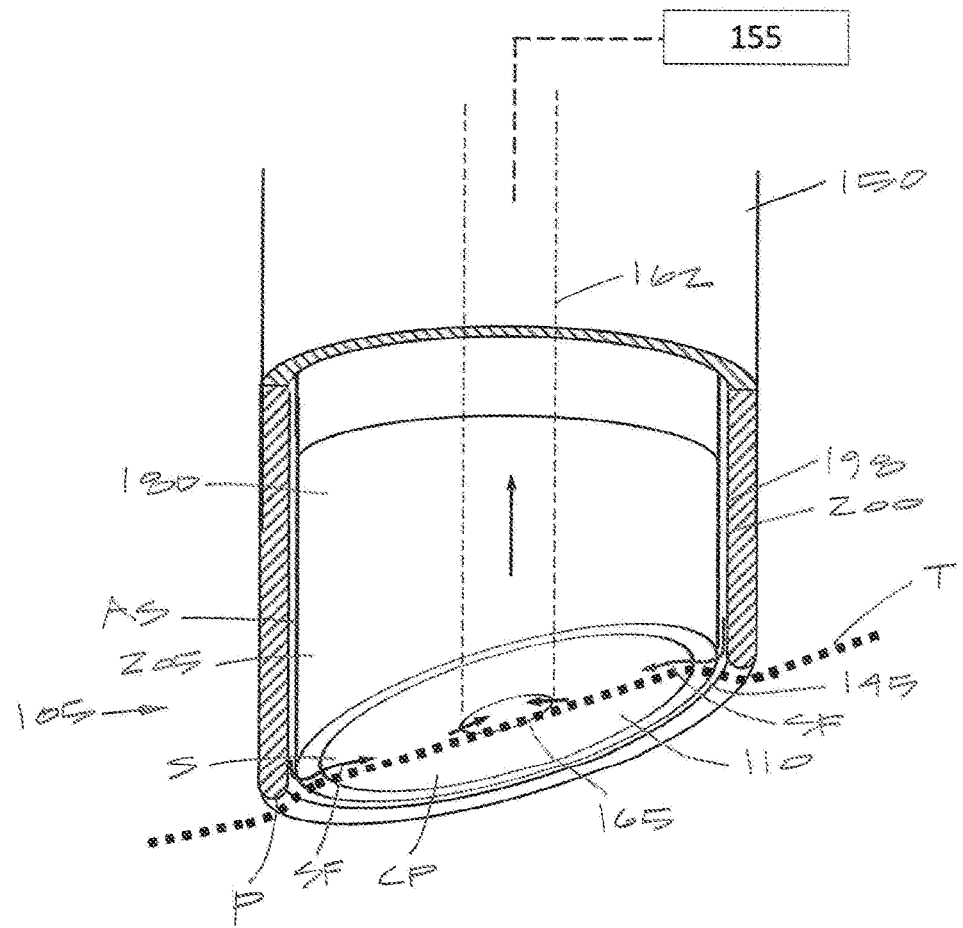
FIG. 4 is a cut-away view of the distal portion of the applicator of FIG. 3, showing targeted skin suctioned into contact with the distal tip and further showing inflow and outflow pathways.
Figure 5:
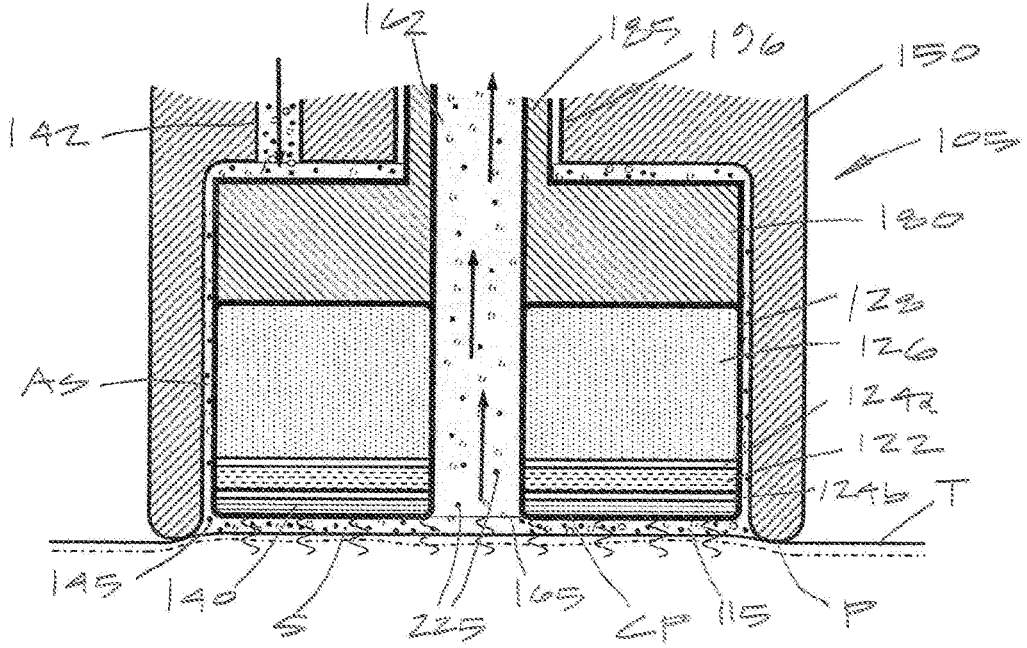
FIG. 5 is an enlarged sectional view of the distal tip of FIGS. 1 and 3-4 illustrating the application of acoustic energy to serum captured in a sealed space between the transducer and the targeted skin.

FIGS. 1 and 2 illustrate a skin treatment system 100 that is adapted for facial treatments, lip treatments, hair loss treatments, or other skin treatments and is adapted to apply serums to a targeted skin surface while contemporaneously using ultrasound to permeabilize the targeted skin surface for more effective penetration of the serums into the targeted skin. The system 100 includes a handpiece or applicator 102 having a longitudinal axis 104 and a distal applicator tip 105 that carries an ultrasound transducer 110 or a plurality of transducers. The ultrasound transducer 110 is adapted for insonation of a continuous flow of a treatment serum 115 that is captured and isolated in an interface comprising a sealed space S between the transducer 110 and the targeted skin T (FIGS. 4-5). Ultrasound energy emitted from the transducer 110 at a selected frequency range and intensity then dimensionally alters acoustically responsive media 120 in the serum 115 (FIGS. 5-6) or being mixed into the serum to create acoustic pressure peaks transmitted from the flow of serum 115 toward the skin which in turn permeabilizes the targeted skin.

Figure 3:
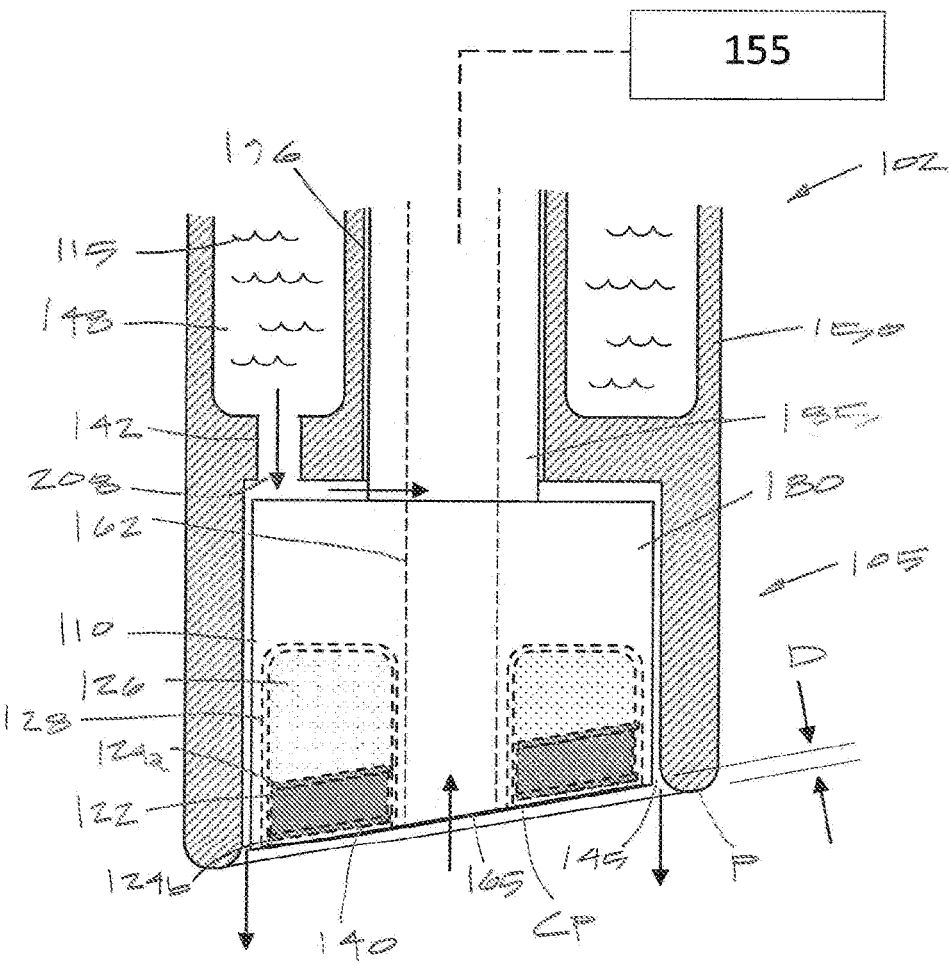
FIG. 3 is an enlarged sectional view of a distal portion of applicator tip of FIG. 1, taken along line 3-3 of FIG. 1, showing an ultrasound transducer and an applicator handle portion with a serum reservoir and inflow and outflow pathways.

Referring to FIGS. 3 and 5, the distal tip 105 of the applicator 102 is shown in enlarged sectional views. The ultrasound transducer 110 comprises an assembly of five typical transducer components as is known in the art, consisting of a piezoelectric crystal element 122 or other element with piezoelectric properties, electrodes 124a and 124b on opposing faces of the piezoelectric element 122, a damping block 126, a housing 128 and an acoustic matching layer 140. As can be seen in FIGS. 1-5, the distal tip 105 has a peripheral portion P that surrounds a central portion CP that comprises the ultrasound transducer 110. As will be described below, the peripheral portion P is adapted to form a seal around the distal tip 105 when in contact with targeted skin T (see FIGS. 4-5).

Referring again to FIG. 5, the acoustic matching layer 140 of the transducer 110 is adapted to minimize the acoustic impedance mismatch between the piezoelectric element 122 and the serum 115 that receives the application of acoustic energy. Acoustic impedance describes how resistant a material is to the transmission of sound waves. When transmitted ultrasound waves encounter a boundary between a first and second media with different acoustic impedances, some acoustic energy will be reflected back and not transmitted into the second media. Thus, the matching layer 140 is designed to have an acoustic impedance that is between that of the piezoelectric element 122 and the fluid serum 115. The matching layer 140 is typically made from a material with specific acoustic properties and often is a polymer that is selected to achieve the desired impedance matching. The thickness, form, shape, and configuration of the composition of the matching layer 140 is also selected to optimize its performance for insonation of captured fluid serum 115. The matching layer 140 reduces the reflection of ultrasound waves at the transducer-serum interface, thus maximizing the transmission of ultrasound energy to targeted acoustically responsive media 120, as further described below.

Figure 6:
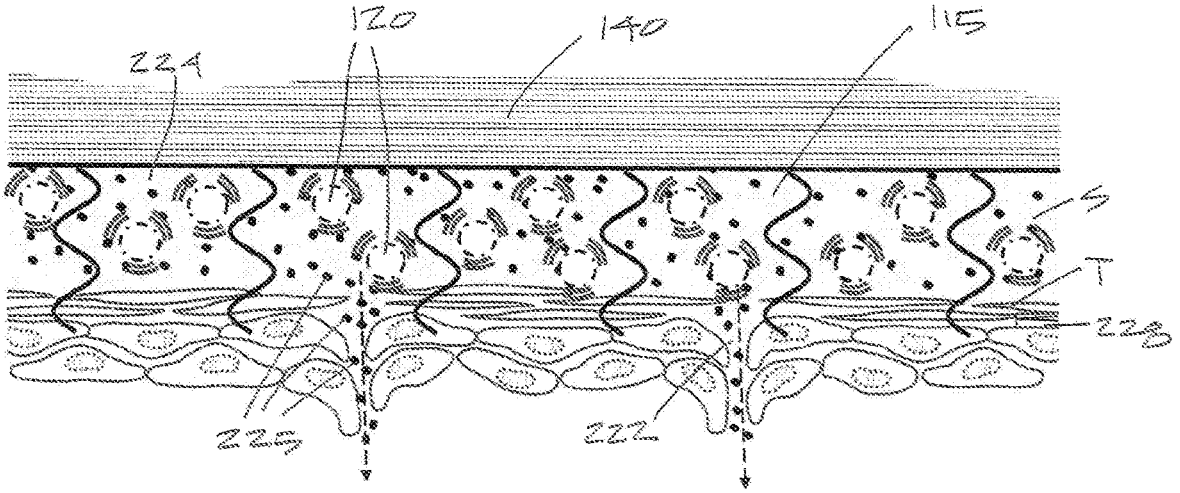
FIG. 6 is an enlarged schematic view of the matching layer of the transducer, the captured serum, and applied acoustic energy causing dimensional changes in acoustically responsive media in the serum, which creates acoustic pressure and loosens the paracellular junctions in the skin to allow active elements of the serum to penetrate the skin surface.

In FIGS. 2-3, it can be seen that the distal tip 105 has a serum inflow channel 142 communicating with an annular inflow port 145 that is coupled to an interior chamber 148 in a handle component 150 of the applicator 102 that carries the serum 115. In the variation of FIGS. 1-3, the applicator 102 is further configured for applying negative pressure to the targeted skin T from a remote negative pressure source 155 in a console 160. The negative pressure source 155 is coupled to an aspiration channel 162 extending through the applicator 102 to an aspiration port or outflow port 165 in or adjacent to the transducer 110. The negative pressure provided at the outflow port 165 is adapted to suction the serum 115 from the interior chamber 148 of the handle portion 150 and provide a continuous flow of serum 115 into and through the interface or sealed space S of the distal tip 105 and targeted skin as further described below (FIGS. 5-6). In another variation described below, a fluid serum source can comprise a remote source coupled to the applicator 102 through flexible tubing.

In the variation of FIGS. 1-3, the transducer 110 is configured for connection to a remote electrical source 170 and controller 175 in the console 160. In a variation, a touchscreen display 176 is provided to adjust operating parameters of the negative pressure source 155 and the ultrasound transducer 110.

Referring to FIGS. 1 and 2, the applicator 102 is adapted for gripping with an operator's fingers for movement over targeted skin T (FIGS. 4-5). In the variation of FIGS. 1 and 2, the skin-contacting surface periphery P of the distal applicator tip 105 is angled relative to the axis 104 of the applicator 102 and is typically round or oval, but other rounded polygonal shapes are possible as well as a tip 105 having a skin-contacting surface that is transverse to the axis 104 of the applicator 102.

In FIGS. 1 and 2, the applicator 102 is shown in assembled and disassembled configurations, respectively. As best seen in FIG. 2, the applicator 102 comprises an assembly of a first component or transducer component 180 and the second handle component 150 that is shaped for gripping by the operator's hand. In the assembled configuration of FIG. 1, the applicator 102 extends from a proximal end 182 to the tissue-contacting distal tip 105.

In the variation of FIGS. 1 and 2, the transducer component 180 is reusable and can be easily cleaned or otherwise sterilized. In this variation, the transducer component 180 that carries the transducer 110 is coupled to an elongated proximal body portion or shaft portion 185 that is configured to extend through the handle component 150 when assembled. As can be seen in FIGS. 1 and 2, a first connector 186 is formed at the proximal end 187 of shaft portion 185. The first connector 186 has electrical contacts 188a and 188b connected to electrical leads that extend through the shaft portion 185 to energize the transducer 110. A flexible conduit 192 is configured to connect the handpiece 102 to the remote negative pressure source 155, electrical source 170, and controller 175. As can be seen in FIGS. 1 and 2, the distal end of the conduit 192 has a second connector 194 adapted to couple to the first connector 186 of the handpiece 102.

Still referring to FIGS. 1 and 2, the handle component 150 is typically a molded plastic with interior chamber 148 that carries a treatment fluid or serum 115. In this variation, the chamber 148 has an annular configuration around a central passageway 196 (FIGS. 2-3) therein that receives the shaft portion 185 of the transducer component 180. The use of an annular chamber 148 is advantageous as a significant volume of serum 115 can then be carried in the handle portion 150, with the volume being at least 5 cc, at least 6 cc, or at least 8 cc. It should be appreciated that the handpiece 102 can be designed in various configurations that provide a first transducer component 180 that is re-usable and a second body or handle component 150 that carries a fluid chamber or reservoir, with such a second body component configured for a single use or for multiple uses. It should be appreciated that the scope of the invention includes a handpiece with a unitary body that carries an ultrasound transducer 110 for coupling with a remote fluid source, wherein such a unitary body is cleanable or sterilizable. Other handpiece variations fall within the scope of the invention and include a transducer body configured to receive a fluid-filled cartridge or handpieces that are configured for selecting a serum flow from an interior chamber in the applicator and/or from a remote reservoir.

Referring to FIGS. 2 to 5, the distal end of the handle component 150 is configured with a cylindrical receiving space 198 that is dimensioned to receive the transducer 110. The receiving space 198 is surrounded by a thin wall 200 with a distal surface that forms the peripheral portion P of the tip 105 with the transducer 110 in the central portion CP of the tip 105 when the handpiece components are assembled. The peripheral portion P extends slightly distally to at least a region of the central portion CP to form a peripheral seal around the distal tip 105, as will be described below. As can be seen in FIGS. 2 and 3, the inflow channel 142 extends from the serum-filled chamber 148 to an opening 208 in the recess 198 in the handle component 150, wherein the annular space AS between the inner surface of recess 198 and lateral surfaces 205 of the transducer 110 forms a distal portion of the inflow channel 142 that extends to annular inflow port 145. In FIG. 4, the serum flow is indicated at arrows SF through the annular space AS. The inner surfaces of the recess 198 and the lateral surfaces 205 of the transducer 110 are dimensioned to allow for a flow of serum through the annular space AS. Alternatively, axial channels can be provided in the inner surfaces of the recess 198 and/or the lateral surfaces 205 of the transducer 110 to provide for serum flows.

Referring to FIGS. 3 and 4, the distal-facing surface or matching layer 140 of the transducer 110 is shown in a variation that is angled relative to axis 104 of the handpiece 102, but the surface 140 may also be transverse to axis 104. In any such configuration, as best seen in FIG. 3, the distal surface of wall 200 that forms the peripheral portion P extends a distance D from 0.2 mm to 2.0 mm distally beyond regions of the central portion CP and distal surface of the transducer 110. In use, the distal tip 105 of handpiece 102 is pressed into an interface with a targeted skin surface T (see FIGS. 4-5), wherein the peripheral portion P is thus adapted to form a seal around the periphery of distal tip 105, which in turn causes negative pressure in the interface with targeted tissue T to draw serum 115 from chamber 148 into the annular space AS between and around the lateral surfaces 205 of the transducer 110 and then into the sealed space S between the transducer 110 and the targeted skin T (FIGS. 4-5). In a variation, the transducer has a matching layer with a surface area of at least 1.0 cm$^2$ and typically a surface area ranging from 1 cm$^2$ to 20 cm$^2$.

Figure 17:
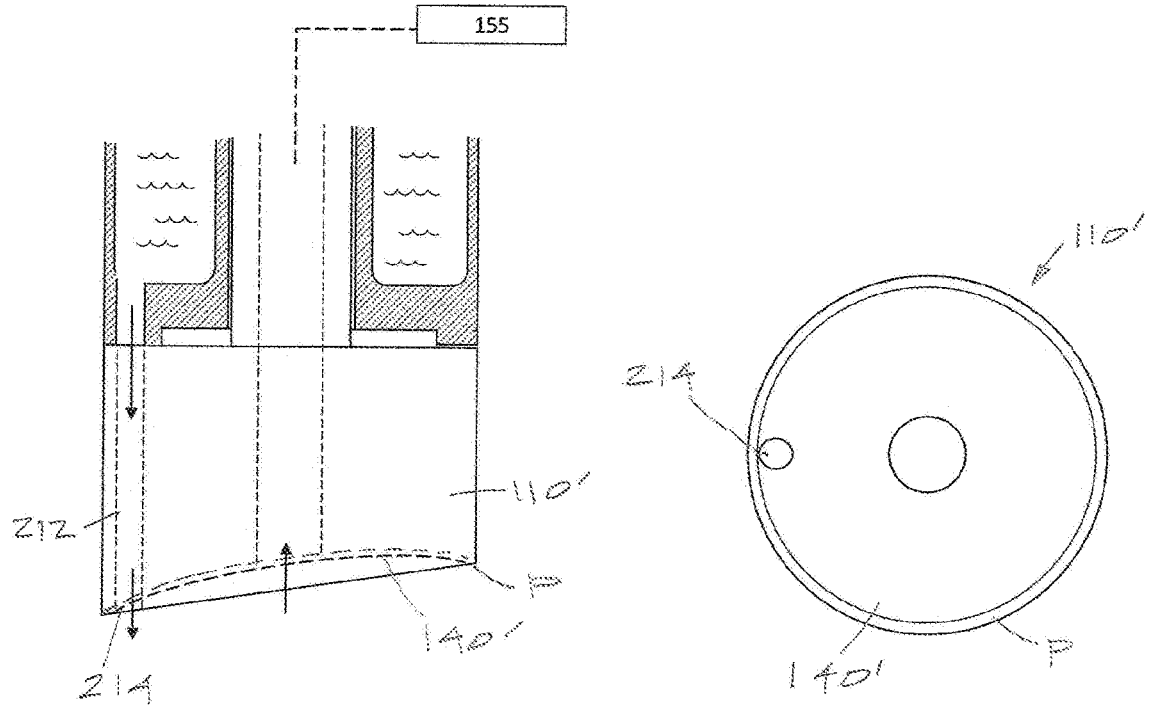
FIG. 17A is a cut-away view of a variation of a distal tip with a transducer component having a concave surface and configured with a serum inflow channel and an aspiration channel therein.
FIG. 17B is an end view of the transducer component of FIG. 17A.

As shown above in FIGS. 1 to 6, the distal-facing matching layer 140 of the ultrasound transducer 110 is flat or planar. Other variations are possible wherein the distal surface of an ultrasound transducer 110' is concave, which includes the surface of matching layer 140' as shown in FIGS. 17A-17B. In another variation, a distal tip of an applicator can carry a plurality of ultrasound transducers with planar surfaces that are angled toward the central axis of the distal tip (not shown). In such variations, the rim or peripheral portion P of the transducer itself is configured to function as a sealing element to provide a peripheral seal against targeted similar to the peripheral portion P of FIGS. 3-5 that forms a seal against targeted skin T. In the variation of FIG. 17A, the serum inflow channel 212 and inflow port 214 are disposed in the transducer 110' rather than in an annular space AS around the transducer as in the variation of FIGS. 1-5.

In FIG. 3, serum flow arrows SF depict the inflow of serum 115 through the annular space AS without targeted skin being shown. FIG. 4 shows the distal tip 105 with serum inflow arrows SF depicting a continuous flow of serum 115 directed through the interface comprising the sealed space S between the matching layer 140 or transducer 110 and targeted skin T. Thus, the ultrasound transducer, the peripheral sealing portion P around a periphery of the ultrasound transducer and the targeted skin T define the sealed space S that captures the serum 115 and receives the application of acoustic energy to cause the dimensional change in the acoustically-responsive media 120 in the serum 115 that in turn creates acoustic pressure peaks that loosen paracellular junctions 222 in the targeted skin T as shown in FIG. 6. The negative pressure causes the continuous circulating flow of serum 115 through the sealed space S and across the targeted skin T between the annular inflow port 145 and the aspiration port 165 in the tip 105, wherein such a circulating flow of serum 115 only occurs when the distal tip 105 is sealed in contact with the targeted skin T.

In general, a method of enhancing permeability of a targeted skin surface comprises applying acoustic energy to a serum captured in a sealed space proximate a distal tip of an applicator wherein the sealed space is defined by (i) an ultrasound transducer in a central portion of the distal tip, (ii) a peripheral scaling portion around a periphery of the distal tip configured to form a seal against targeted skin, and (iii) the targeted skin, wherein applying acoustic energy from the ultrasound transducer causes a dimensional change in acoustically responsive media in the captured serum thereby creating acoustic pressure that loosens paracellular junctions in the targeted skin.

Referring to FIGS. 5 and 6, the topical composition or serum 115 for skin treatments and lip treatments is shown in the sealed space S between the matching layer 140 of transducer 100 and the targeted skin T. The serum 115 comprises a dermatologically acceptable carrier 224 that carries or is mixed with an effective amount of an acoustically responsive media 120 that is adapted to change dimension or expand in dimension in response to acoustic energy transmitted from the transducer 110 at a frequency range of 0.25 MHz to 10 MHZ. The dimensional change of the acoustically responsive media 120 creates acoustic pressures in the serum 115, which, in turn, applies mechanical forces to the targeted skin T. Such mechanical forces can include forces caused by shock waves or microstreaming from cavitation in some forms of acoustically responsive media 120, which then loosens paracellular junctions 222 to cause permeabilization of the targeted skin T to permit agents or active elements 225 to penetrate layers of the stratum corneum 228 as shown schematically in FIG. 6.

In a variation, as depicted schematically in FIGS. 5 and 6, the acoustically responsive elements 120 can comprise microbubbles having a polymeric shell structure with a single outer shell layer or multiple shell layers. An inert gas is carried in the core of the shell or shell layers. In a variation, the microbubbles can comprise albumin shells around an inert gas, such as air or perfluoropropane. The microbubbles can be fabricated, as is known in the art of making ultrasound contrast agents. (See Yusefi, H. and Helfield, B.; "Ultrasound Contrast Imaging: Fundamentals and Emerging Technology," Front. Phys. 17; February 2022). Such microbubbles can range in size from 400 nm to 50 microns and typically can be from 5 microns to 50 microns. The acoustic energy applied to such microbubbles can cause stable cavitation or inertial cavitation of the microbubbles in the serum 115 to create pressure peaks in the continuous flow of serum 115 to thereby loosen paracellular junctions 222 and cause permeabilization of the targeted skin T.

In another variation, the acoustically responsive media 120 can comprise nanoscale, phase-change particles that are known as phase-change contrast agents (PCCAs). Such nanoparticles can be phase-transitioned into highly echogenic elements by means of ultrasound energy, which in turn causes acoustic pressures in the serum. The application of ultrasound energy to such nanoparticles causes the phenomenon of acoustic droplet vaporization to produce bubbles that have been investigated for both therapeutic applications and imaging. In one variation, the droplet vaporization results in acoustic pressure peaks and mechanical forces at a nanoscale or micro-scale that can permeabilize anatomical and/or functional membranes such as a subject's targeted skin. FIG. 6 schematically illustrates acoustic droplet vaporization or microbubble cavitation that results in mechanical forces that loosen paracellular junctions 222 and cause permeabilization of the targeted skin T to allow agents or active elements 225 to penetrate the targeted skin T. The use of acoustically-responsive phase-change nanoparticles and types of nanoparticles potentially useful for skin permeabilization are described in S. Zullino et al., From Micro- to Nano-Multifunctional Theranostic Platform: Effective Ultrasound Imaging Is Not Just a Matter of Scale; Molecular Imaging; Volume 17, January-December 2018, and T. Matsunaga et al., Phase-Change Nanoparticles Using Highly Volatile Perfluorocarbons: Toward a Platform for Extravascular Ultrasound Imaging; Theranostics, December 2012: 1185-98.

In another variation, the acoustically responsive media 120 can comprise air bubbles BB or bubbles of another inert gas that are introduced into the serum in the applicator, as will be further described below in FIGS. 15 and 16.

In another aspect, a method of applying a serum to a targeted skin surface comprises providing a continuous flow of a serum in an interface between an ultrasound transducer and targeted skin, applying acoustic energy from the transducer to the flow of serum in the interface, and causing dimensional changes in acoustically-responsive media 120 in, or adjacent to, the serum to thereby create acoustic pressure peaks that in turn loosen paracellular junctions 222 in the targeted skin to enhance penetration of the serum 115 in the targeted skin. The acoustic pressure has peak pressures of at least 0.1 MPa, at least 0.5 MPa, or at least 1.0 MPa.

The effective amount of acoustically responsive media 120 in the form of microbubble or nanoscale contrast agents is between 0.01% and 10% by weight of the serum 115. The dermatologically acceptable carrier 224 can comprise humectants, emollients, and occlusives, as are known in the art. In a variation, the serum 115 or topical composition includes agents or active elements 225 for plumping tissue, such as is known in the art for treating lips and skin. The active elements 225 can include an effective amount of a capsicum extract or resin from Capsicum annuum or capsicum frutescens. Additionally or, alternatively, the serum 115 can include an effective amount of at least one of benzyl nicotinate and methyl nicotinate. In a variation, the active elements 225 can be selected from the group of hyaluronic acid or derivatives, fractions or fragments thereof, glycerine, ectoin, niacinamide, propylene glycol, hydrogenated lecithin, capric triglyceride, cholesterol, linoleamidopropyl Pg-dimonium chloride phosphate, tocopheryl acetate, tocopherol, vitamin C, Mentha piperita oil, glyceryl stearate, dimethicone, synthetic beeswax, cetyl alcohol, oleth-2, caprylyl glycol, caprylhydroxamic acid, paraffinum liquidum, persea gratissima oil, mica, Simmondsia chinensis seed oil, ethylhexyl palmitate, tribehenin, sorbitan isostearate, palmitoyl oligopeptide, tocopheryl acetate, pentaerythrityl tetraisostearate, silica dimethyl silylate, sodium chondroitin sulfate, atelocollagen, phenoxyethanol, lactic acid, mandelic acid, and glycolic acid.

To use the system 100, the operator typically can select a negative pressure on the touchscreen display 176, as shown in FIGS. 1 and 2. The operator also can select an operating mode on the touchscreen display 176 among various energy levels and duty cycles for ultrasound transducer 110 to provide the peak acoustic pressures described above.

Figure 7A:
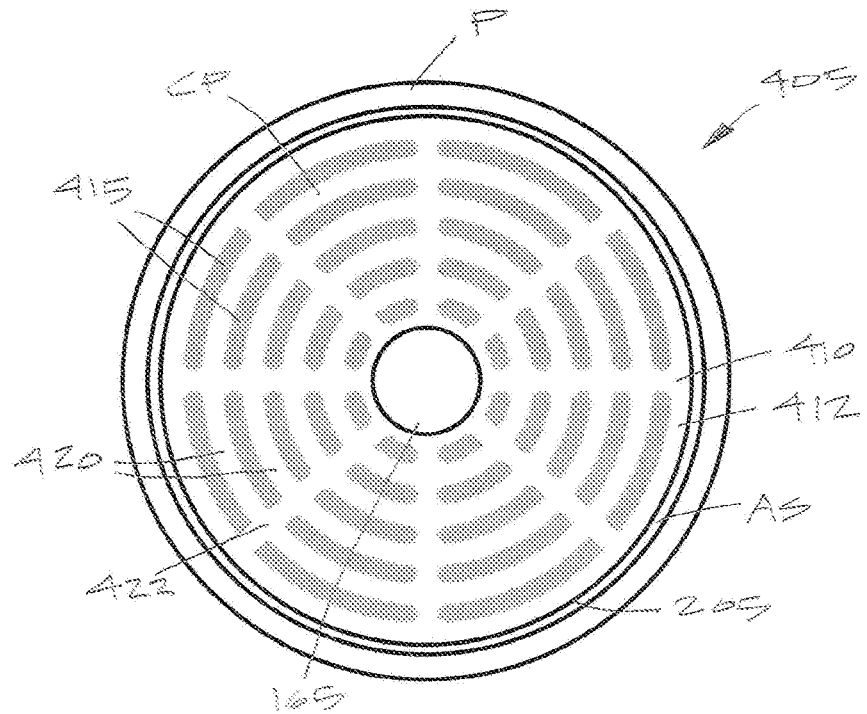
FIG. 7A is an end view of another variation of a distal tip with a non-smooth surface wherein the matching layer is configured with spacing elements comprising projecting ridges for spacing portions of the transducer apart from targeted skin to capture serum in recesses between the projecting ridges.
Figure 7B:
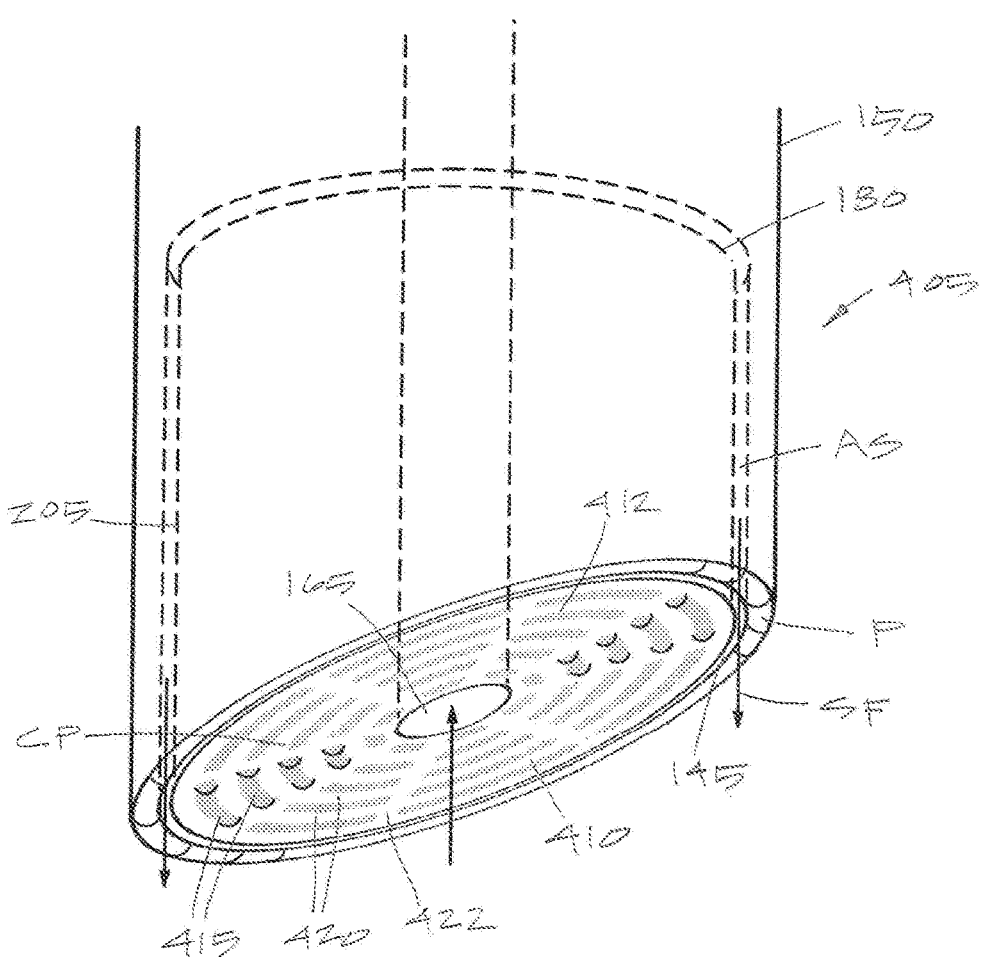
FIG. 7B is a perspective view of the distal tip of FIG. 7A showing the spacing elements and fluid inflow and outflow pathways.
Figure 8:
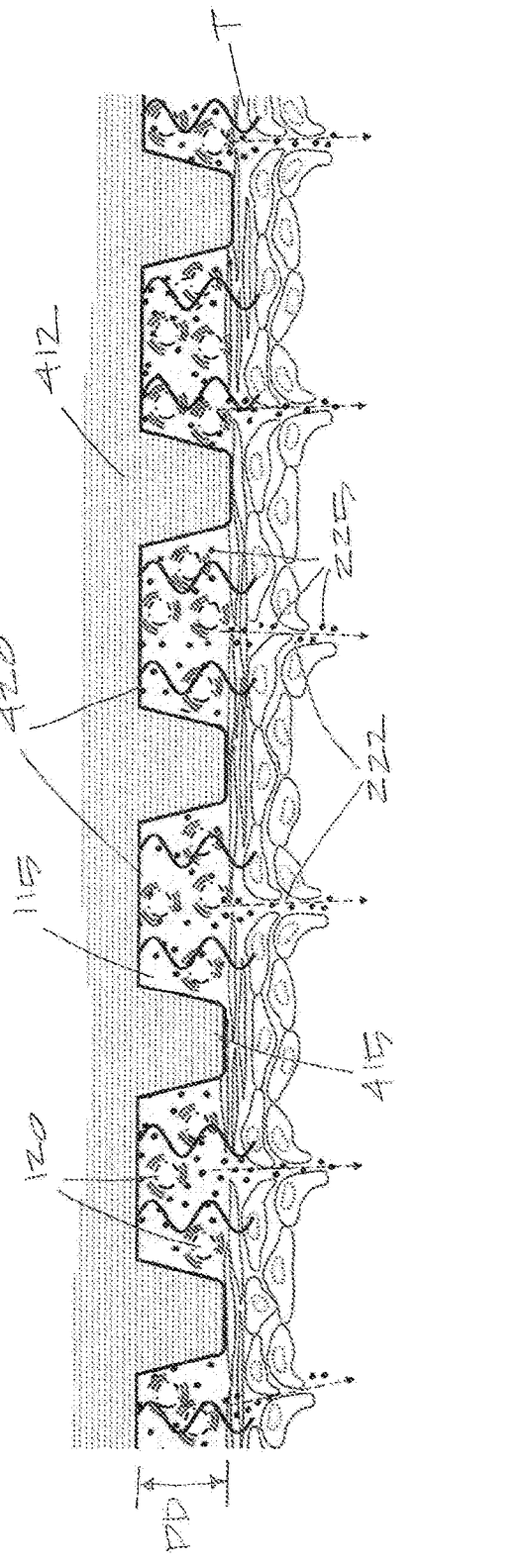
FIG. 8 is an enlarged schematic view of the matching layer of the transducer of FIGS. 7A-7B showing spacing elements contacting skin, serum captured in the recesses, and applied acoustic energy causing dimensional changes in acoustically responsive media in the serum, which creates acoustic pressure and loosens the paracellular junctions in the skin to allow active elements of the serum to penetrate the skin.

FIGS. 7A, 7B, and 8 illustrate a variation of an applicator distal tip 405 and ultrasound transducer 410 that is similar to the variation of FIGS. 1-3. The distal tip 405 again has the same transducer component 180 and handle component 150 as the variation of FIGS. 1-6. The serum inflow channel again consists of the annular space AS around the lateral surfaces 205 of the transducer component 180. The variation of FIGS. 7A-7B differs in that the distal surface of the transducer 410 has a distal matching layer 412 that is not as smooth as in the previous variation of FIGS. 1-6. In the variation of FIGS. 7A-7B, the peripheral portion P again surrounds the central portion CP to define the sealed space S adapted to capture the continuous flow of serum 115, however, in the variation of FIGS. 7A-7C, the central portion CP and the surface of transducer 410 are configured with spacing elements 415 that comprise a plurality of projecting features that are configured to contact targeted skin (see FIG. 8) to maintain a non-collapsed sealed space S (cf. FIGS. 4-5) for capturing a serum flow SF having an effective depth and volume for receiving acoustic energy to thereafter apply acoustic pressure to the targeted skin T. The surface of transducer 410 thus has recessed regions 420 intermediate or adjacent to the projecting spacing elements 415, which capture the flow of serum 115.

In FIGS. 7A and 7B, a variation of projecting spacing elements 415, have a partly annular configuration with gaps 422 therein to allow for circulation of serum 115 from the annular inflow port 145 to the central aspiration port 165. It should be appreciated that the projecting spacing elements 415 can be bumps, linear ridges, annular ridges, or any other form of projecting features that function as a spacer between the transducer 410 and the targeted skin. The distalmost surface of any spacing element 415 can be rounded or sharp. The bottom of the recesses 420 between projecting spacing elements 415 can be rounded or angular.

Figure 9A:
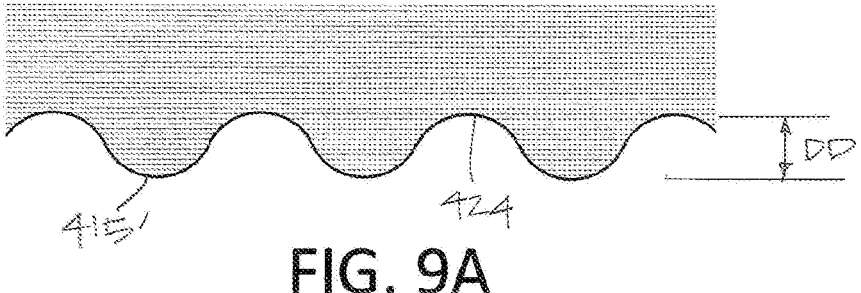
FIG. 9A is a sectional schematic view of a matching layer of a transducer with spacing elements comprising rounded undulations or bumps.
Figure 9B:
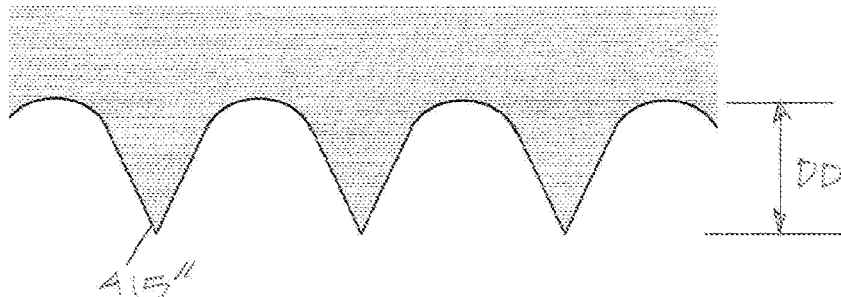
FIG. 9B is a sectional view of another matching layer of a transducer with spacing elements comprising ridges or projections having a sharp apex.

FIG. 8 is a sectional view of projecting spacing elements 415 of the transducer matching layer 412 of FIGS. 7A-7B illustrating rounded bumps or a ridge features. Projecting spacing elements 415 can comprise at least one of ridges, bumps, or any distalmost surfaces that are distal from adjacent recesses 420, where such recesses can comprise channels, grooves, dimples, bores, and the like. FIGS. 9A and 9B are sectional views of projecting spacing elements 415' that are rounded with a rounded recess 424. FIG. 9B is a sectional view of projecting spacing elements comprising a sharp bump or a ridge 415".

The space between the spacing elements 415 is selected to be small enough to prevent the targeted skin surface from being suctioned into the recess, and typically the dimension between the apex of each spacing element is less than 3.0 mm, less than 2.0 mm, or less than 1.0 mm. The depth DD of each recess is at least 0.5 mm. In a variation, the recessed space in the central portion CP of a distal tip comprises at least 25% of the total surface area of the distal tip, at least 40% of the surface area of the distal tip, or at least 60% the surface area of the distal tip.

Figure 10:
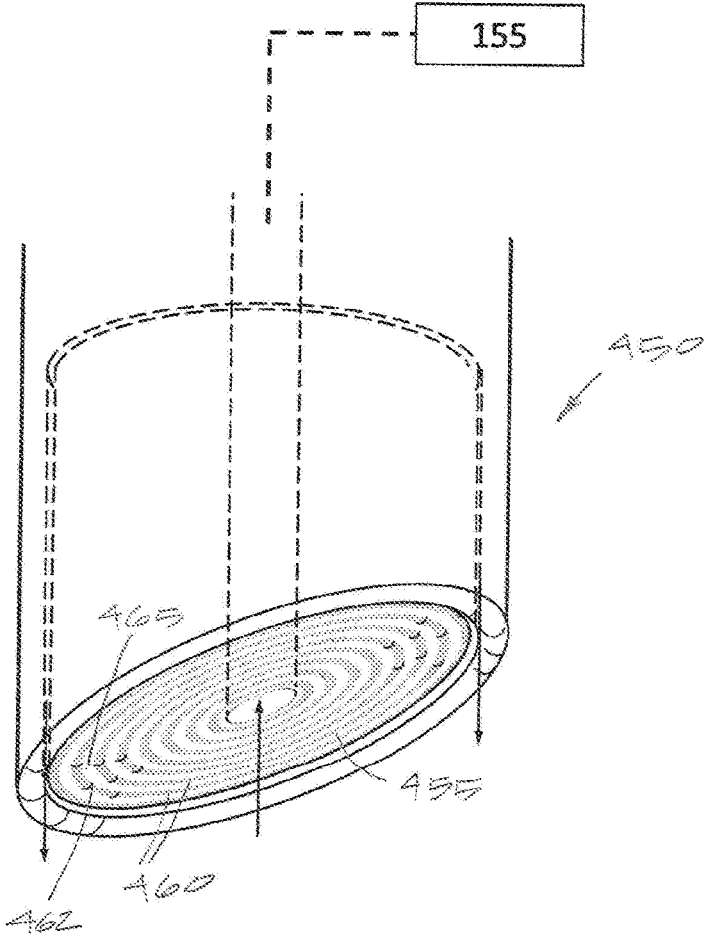
FIG. 10 is a perspective view of an alternative variation of a distal tip and inflow and outflow pathways wherein the matching layer is configured with fully annular ridges and recesses wherein the ridges comprise flow-restricting elements to restrict a direct flow of serum between the inflow port and the aspiration port.
Figure 11:
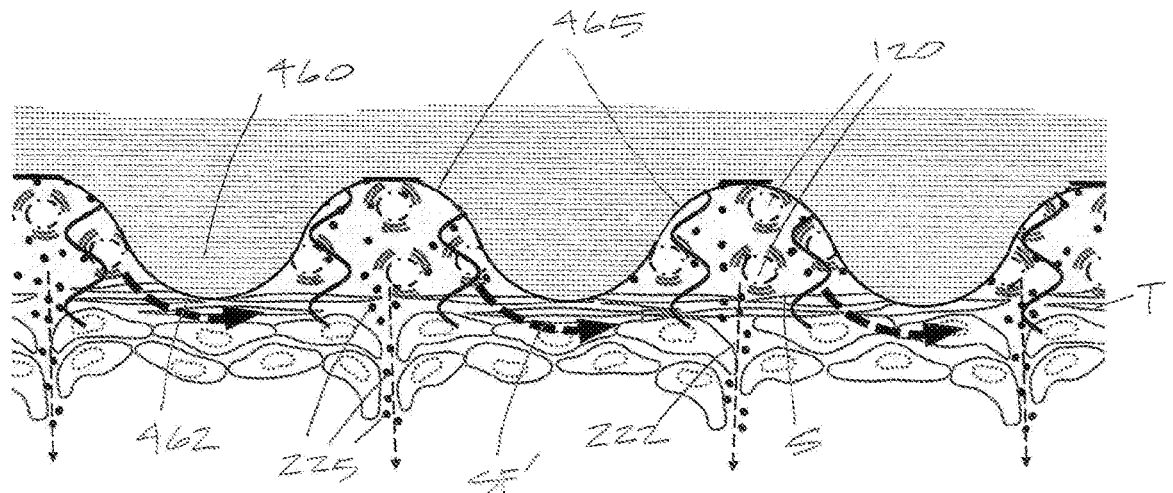
FIG. 11 is an enlarged schematic view of the matching layer of FIG. 10 showing ridges contacting skin, serum captured in the recesses, and applied acoustic energy causing dimensional changes in acoustically responsive media in the serum wherein flows of serum are restricted and pass over the apex of each ridge and penetrate the skin as the flow of serum is drawn toward the aspiration port.

In another variation, a distal applicator tip 450 is shown in FIGS. 10 and 11 with transducer 455 configured with spacing elements 460 that comprise a plurality of fully annular projecting ridges, each with an apex 462, and thus defining annular channels or recesses 465 therebetween that are adapted to capture serum 115 for insonation. In this variation, the negative pressure source 155 applies negative pressure to the sealed space S (FIG. 11) to again cause a continuous flow of serum 115, as described previously. The annular spacing elements 460 function as flow-restriction elements to restrict or direct the flow of serum 115 but not to stop such serum flows. As shown in FIG. 11, the serum flows at arrows SF' are impeded as the flow moves over the apex 462 of projecting ridges, which is advantageous as the serum may be forced into the targeted skin at the apex 462 of each ridge following loosening of extracellular junctions as the tip 450 is translated over targeted skin T.

Figure 12:
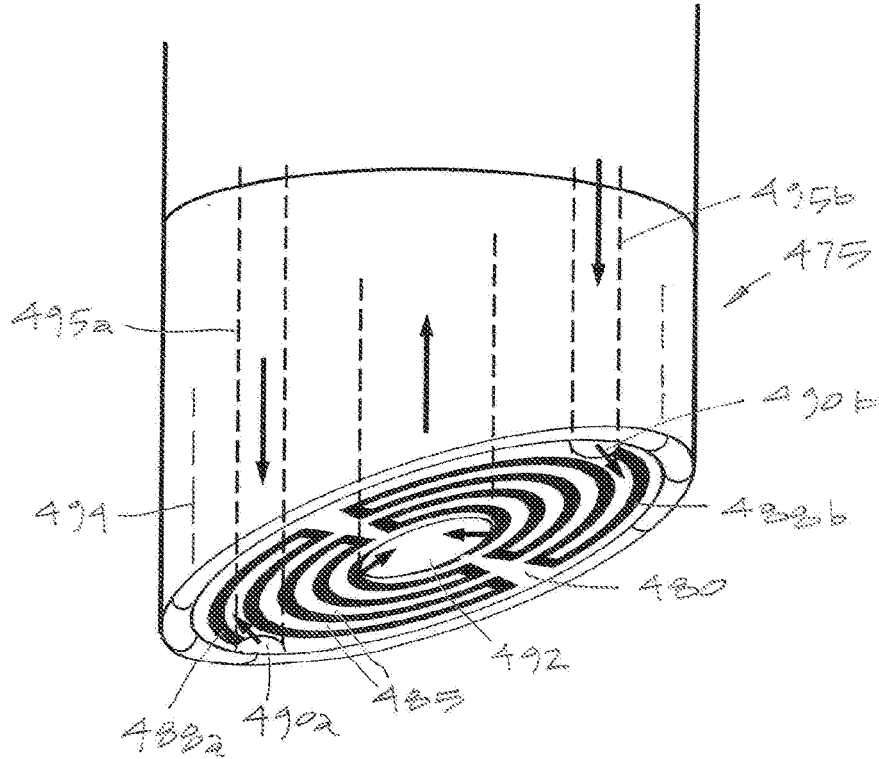
FIG. 12 is a perspective view of another variation of a distal tip and inflow and outflow pathways wherein the matching layer is configured with circuitous flow-directing channels to direct and restrict the flow of serum between the inflow port and the aspiration port.

In another variation shown in FIG. 12, a distal tip 475 has a transducer 480 configured with ridge-like spacing elements 485 that define first and second flow-restricting or flow-directing channels 488a and 488b between the spacing ridge elements 485, wherein the channels 488a, 488b follow a circuitous path between inflow ports 490a and 490b and a central aspiration port 492. In such a variation, the flow-restricting channels 488a, 488b maintain the serum 115 within the interface and sealed space S (cf. FIGS. 4-5) between the transducer 480 and the targeted skin T for a longer time interval, which is advantageous. By restricting the circulating flow of serum 115, the circuitous channels 488a, 488b provide a longer time interval in which the serum is in the interface for insonation, which also can provide an increased penetration of serum into skin from a selected volume of serum rather than allowing a freer flow of the serum between the inflow ports 490a. 490b and the aspiration port 492. In this variation, the lateral surfaces 494 of the transducer 480 are configured with two inflow channels, 495a and 495b, extending to the inflow ports 490a and 490b. It should be appreciated a distal tip can be configured with 1 to 100 such flow-restricting channels, which can take various forms such as maze-like channels, spiraling channels, serpentine channels, and the like with the variation of FIG. 12 shown as a non-limiting example.

Figure 13:
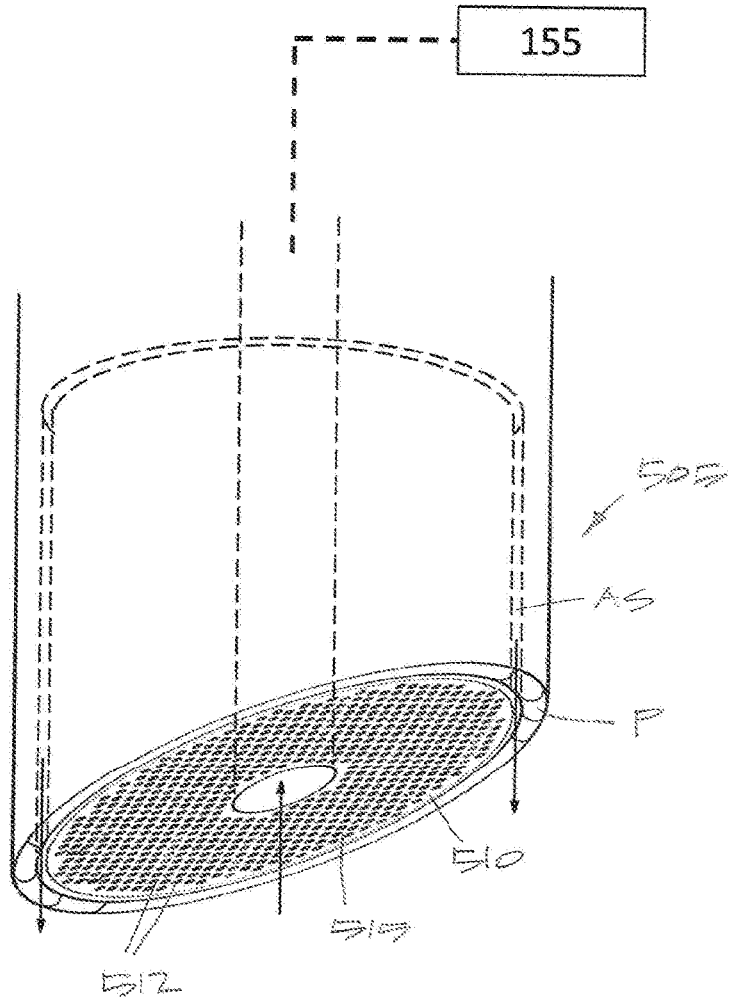
FIG. 13 is a perspective view of another variation of a distal tip and inflow and outflow pathways wherein the matching layer is configured with a plurality of small diameter pockets or recesses configured to capture serum for insonation.
Figure 14A:
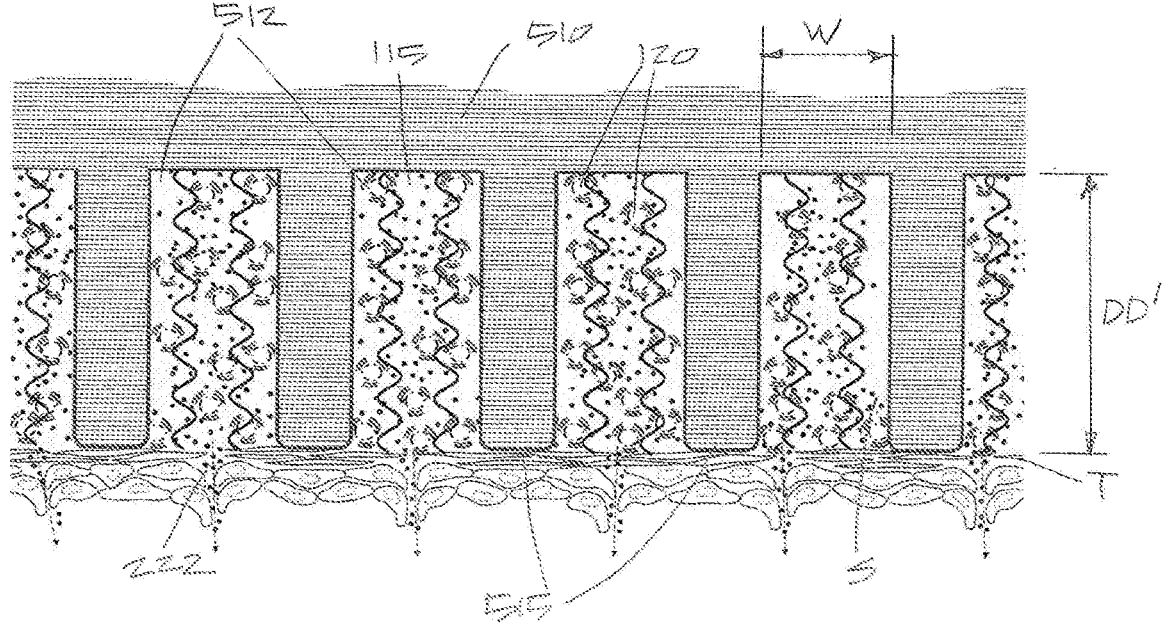
FIG. 14A is an enlarged schematic view of the matching layer of FIG. 13 showing serum captured in the small diameter recesses and applied acoustic energy causing dimensional changes in acoustically responsive media, creating acoustic pressure and loosening the paracellular junctions in the skin surface.
Figure 14B:
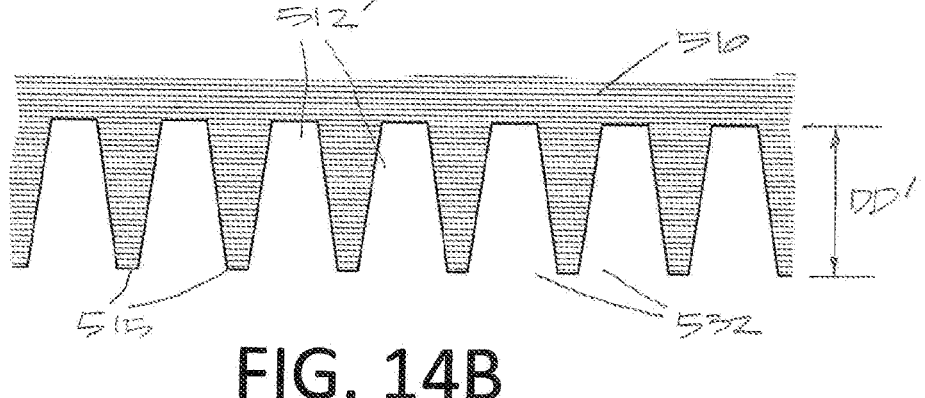
FIG. 14B is a sectional schematic view of a matching layer of a transducer similar to that of FIGS. 13 and 14A with small diameter recesses that taper in the proximal direction.
Figure 14C:
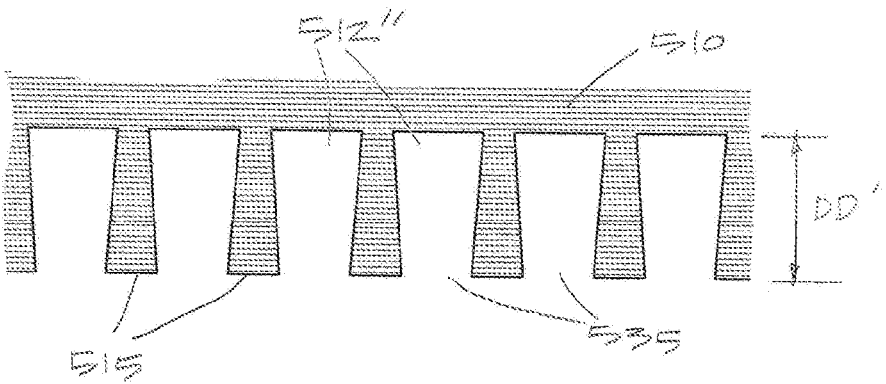
FIG. 14C is a sectional schematic view of a matching layer of a transducer with small diameter recesses that taper in the distal direction to capture serum and can cause a venturi effect to increase acoustic pressures.

Another variation is shown in FIGS. 13 and 14A, wherein an applicator includes a distal tip 505 and transducer 510 configured with a plurality of small, deep axial recesses or pockets 512 in, or adjacent to, the transducer wherein the skin-contacting spacing portion 515 that maintains the serum 115 in a non-collapsed space away from targeted skin comprises a distalmost surface of transducer 510 intermediate the pockets 512. Thus, the sealed space S between the transducer 510 and targeted skin comprises the plurality of pockets 512. The inflow of serum 115 is provided through the annular space AS around the transducer 510, as described previously. In this variation, the pockets 512 are configured with a substantial depth relative to the pocket diameter to maintain the serum 115 in the interface for insonation, which further can provide an increased penetration of serum 115 into targeted skin, as shown in FIG. 14A. Thus, deep pockets 515, as shown in FIG. 14A function as a flow-restricting feature to maintain serum 115 in a plurality of recesses for insonation, which in turn can loosen extracellular junctions 222 and enhance serum penetration into the targeted skin. It should be appreciated that the deep axial recesses can have the form of a cylindrical pocket, as shown in FIG. 14A, but the scope of the invention includes such deep recesses in any channel form, such as annular channels, radial channels, spiral channels, serpentine channels, free-form channels, and the like. The depth DD' of such deep recesses can range from 0.5 mm to 5 mm (FIGS. 14A-14C). The diameter or width W of such deep recesses can be 2 mm or less.

In the variation of FIGS. 13 and 14A, the deep axial recesses 512 can be formed directly in a matching layer of the transducer as described above, or the axial recesses 512 can be formed in a detachable component of the applicator tip 505 that can detachably fitted to the tip 505 to be in contact with the transducer 510.

FIG. 14B is an enlarged sectional view of a surface of transducer 510 and matching layer 522, similar to that of FIGS. 13-14A configured axial recesses 512' that are tapered toward a larger open end 532. FIG. 14C illustrates another similar variation with axial recesses 512" that are tapered toward a smaller open end 535 wherein acoustic energy applied to serum in the recesses can be accelerated by the tapered channel to increase acoustic pressures applied to targeted skin.

Figure 15:
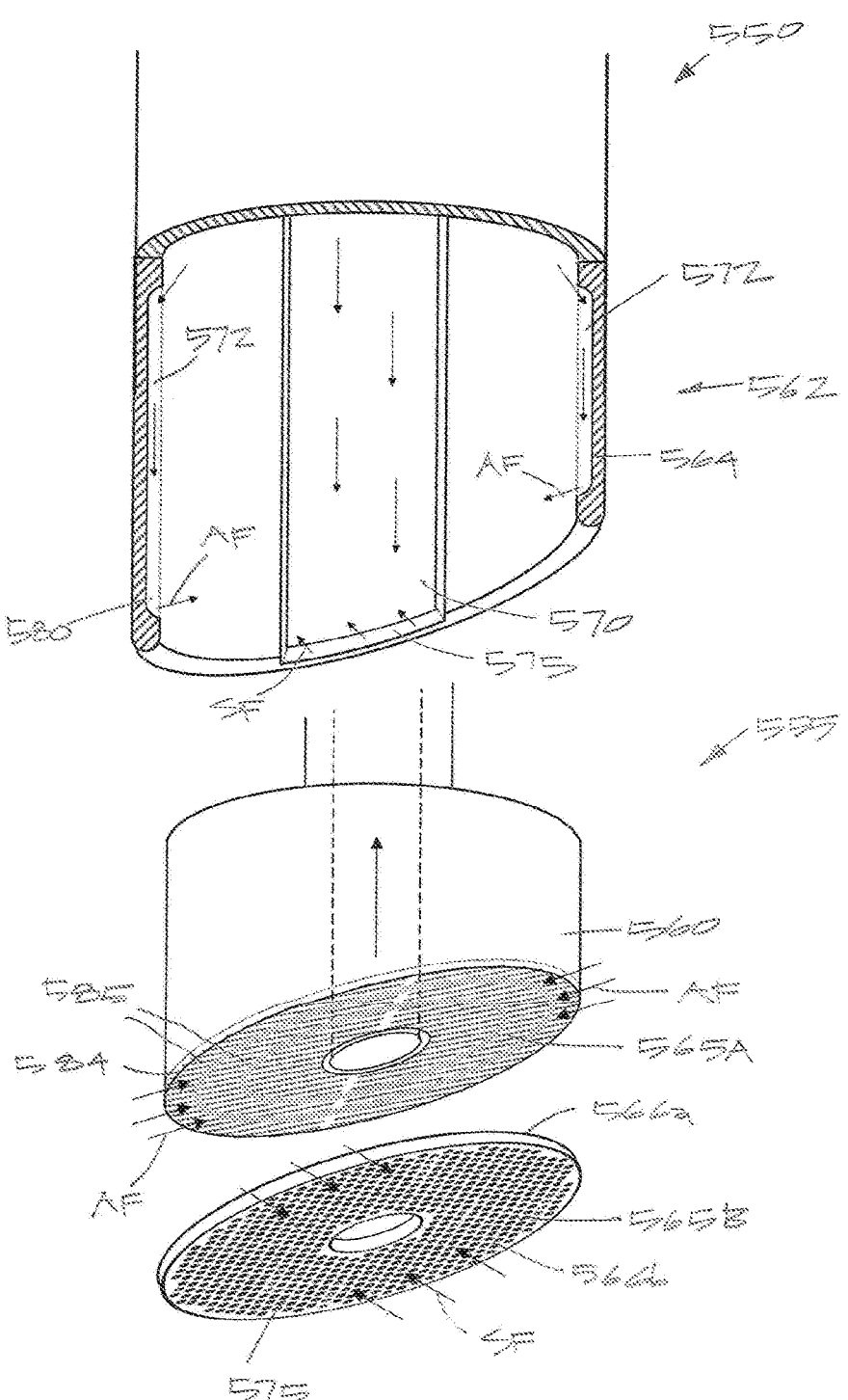
FIG. 15 is another distal tip of an applicator with first and second matching layers in an exploded view with a first set of inflow channels for delivering serum and a second set of inflow channels for introducing air or another gas to mix with serum and to function as an acoustically responsive media in the serum to create acoustic pressures.
Figure 16:
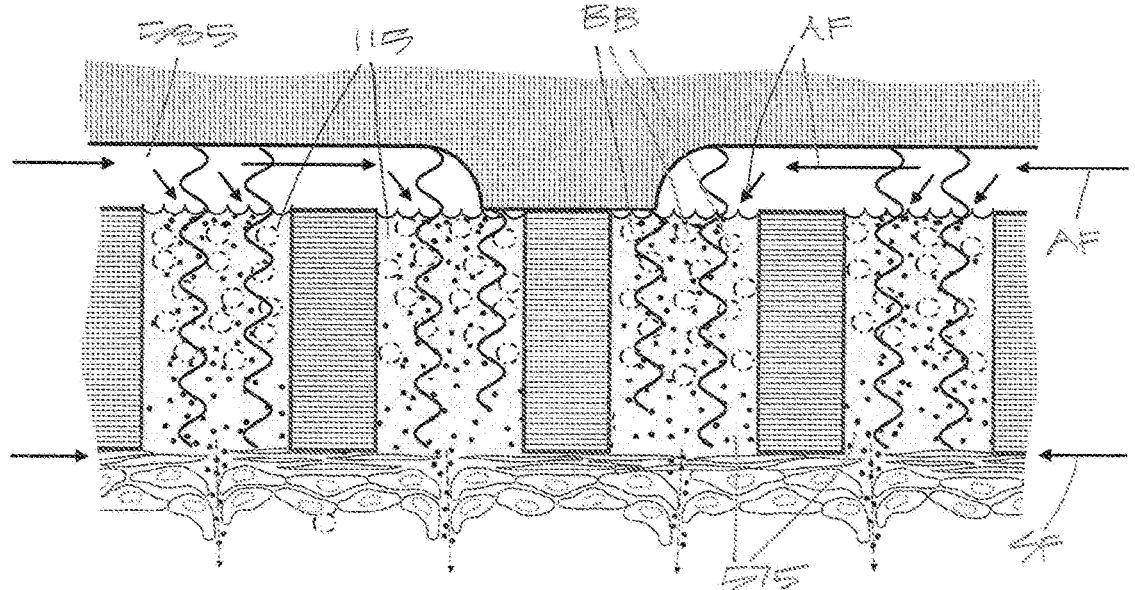
FIG. 16 is an enlarged schematic view of the matching layer of the transducer of FIG. 15 showing serum and a gas introduced into recesses in the first and second matching layers where acoustic energy assists in mixing the inflows to provide gas bubbles that can be insonated to cause dimensional changes in the bubbles to create acoustic pressures and loosen the paracellular junctions.

FIGS. 15 and 16 illustrate exploded and sectional views of other variations of applicator 550 and distal tip 555 carrying transducer 560. In this variation, the distal tip includes the distal end of a handle portion 562 with a thin wall 564 that receives the transducer 560. The transducer 560 has a distal acoustic transmitting surface comprising a first proximal matching layer, 565A, and a second distal matching layer, 565B, shown in an exploded view. The distal matching layer 565B has a proximal surface 566a and distal surface 566b that contacts the targeted skin as described above as a spacer element. The wall 564 of the handle portion 562 is configured with a first set of inflow channels 570 for providing serum inflows indicated at arrows SF. The handle portion 562 is further configured with a second set of inflow channels 572 that are configured to introduce air or an inert gas into the distal tip 555.

The first set of inflow channels 570 comprises axial channels in the wall 564 of the handle portion 562 as described previously to deliver serum 115 from a serum source, such as an interior chamber in the handle portion 562 or a remote source (cf. FIGS. 1-2). The variation of FIG. 15 has a set of two opposing inflow channels 570 with inflow ports 575 around the distal surface of the distal matching layer 565B. The distal matching layer 565B has a plurality of recesses 575 therein similar to the variation of FIGS. 13 and 14A that extend entirely through the proximal and distal surfaces 566a, 566b of the matching layer 565B. The serum flow is indicated by arrows SF in FIG. 15.

Still referring to FIG. 15, the second set opposing inflow channels 572 are adapted to provide a flow of air or another inert gas such CO2 to the distal tip 555 to form air bubbles BB in the serum 115 introduced through the inflow channels 570 (FIG. 16). The airflow or other gas flow is indicated by arrows AF in FIGS. 15 and 16. Thus, the introduced air or other gas, when mixed into or adjacent to the serum 115, introduces an acoustically-responsive media in the form of bubbles microbubbles BB in the serum, which will be dimensionally altered by acoustic energy to thereby create the acoustic pressures as described above to permeabilize targeted skin. In FIG. 15, the inflow channels 572 extend to inflow ports 580 around the outer edge 584 of the proximal matching layer 565A. The proximal matching layer 565A has a plurality of recesses 585 in its distal surface 588 that distribute the air flow AF over the proximal surface 566a, the distal matching layer 565B to introduce the airflow AF into the recesses 575 of distal matching layer 565B and to thereby mix the airflow AF with the serum flow SF captured in the recesses 575. The serum may be introduced on either the proximal surface 566a or distal surface of the distal matching layer 565B. As shown schematically in FIG. 16, the air bubbles BB in the serum 115 comprise the acoustically responsive media and can function similarly to the acoustic responsive media 120 in FIGS. 6, 8 and 14. In a variation, the bubbles BB are infused into the serum as described above, wherein the serum additionally carries the phase change nanoparticles as described in earlier variations to provide multiple forms of acoustically responsive media in the serum.

In another variation, an alternative type of proximal matching layer 565A of FIGS. 15-16 can be used that comprises a polymer or ceramic microporous material with the ability to allow air or gas flow therethrough while preventing serum penetration into the material. Various hydrophobic materials known in the art can be designed with a pore size and surface chemistry to create a barrier to the liquid serum while remaining permeable to air or gas. These materials also then would provide small cross-section channels for airflow to provide small diameter bubbles in the serum. A type of material for this purpose is polytetrafluoroethylene (PTFE), which is known for its hydrophobic properties. In this aspect of the invention, the distal tip comprises an ultrasound transducer with a first, proximal matching layer having microchannels or micropores configured to introduce a gas therethrough from a source of gas and a second, distal matching layer with passageways extending therethrough for receiving a liquid serum from a serum source, where the air and serum are mixed resulting in air bubbles in the serum which then function as acoustically responsive media in the serum.

In the variation of FIGS. 15-16, the source of air or gas to provide the airflow AF can be ambient air at the exterior or interior of the applicator or a positive pressure source such as a pressurized cartridge or a pump in the applicator or remote from the applicator. In a variation, the negative pressure source 155 can serve the dual function of drawing serum 115 into the sealed space S at the distal tip 555 as well as drawing air into the distal tip when sealed against targeted skin.

In the variation of FIGS. 15 and 16, the process of insonation is known for mixing air bubbles into a fluid by means of ultrasonic cavitation, which involves the creation and controlled collapse of small gas bubbles, such as air in a liquid with high-frequency ultrasound waves. Frequencies ranging from 100 kHz to 5 MHz may be used to produce such cavitation. Such cavitation will cause acoustic pressures as described above for permeabilizing targeted skin. In another variation, the serum may be carbonated, as is known in the art of carbonating water and other fluids.

In this aspect of the invention, a method of applying a serum to a skin surface comprises introducing a continuous flow of a serum and a continuous flow of a gas into an interface between an ultrasound transducer and the skin, applying acoustic energy from the transducer to the flows of serum and gas to thereby cause a dimensional change in the gas mixed in the serum to create acoustic pressure peaks that loosen paracellular junctions in the skin to enhance penetration of the serum in the skin.

Figure 18:
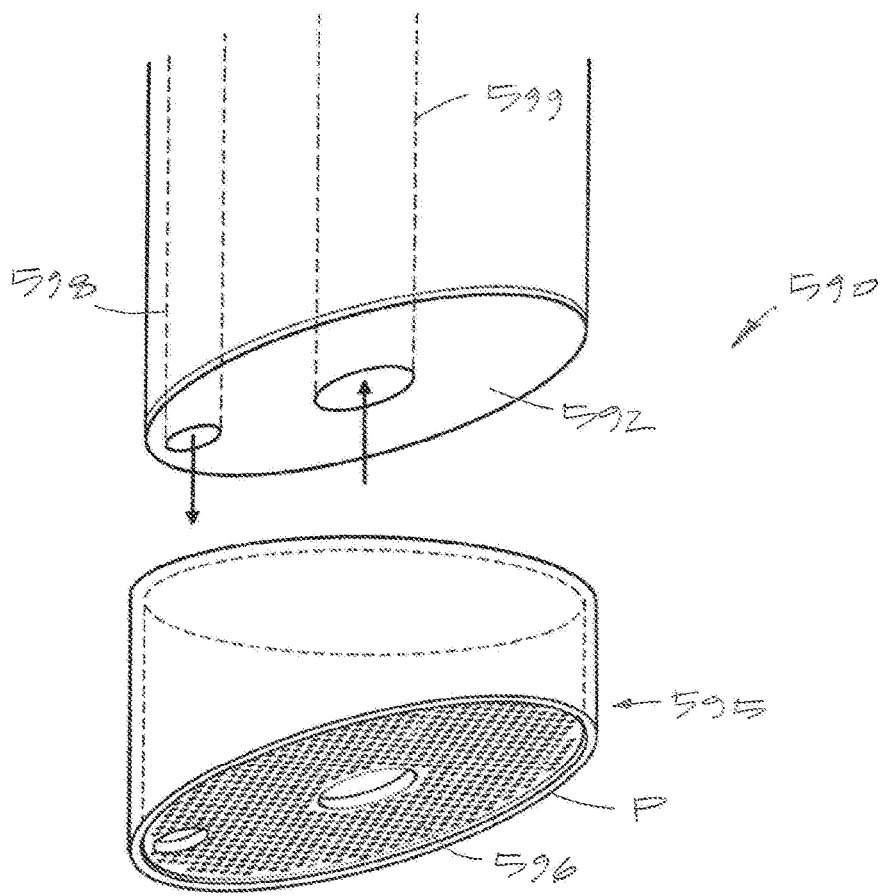
FIG. 18 is an illustration of an ultrasound transducer with a smooth surface for case of cleaning with a de-mated single-use additional matching layer that comprises a molded polymer that can be fitted over a distal portion of the transducer.

FIG. 18 is an illustration of another variation of a distal tip 590 with an ultrasound transducer 592 that has a distal matching layer 594 with a smooth surface for ease of cleaning. The variation of FIG. 18 includes a single-use additional matching layer component 595 that can be fitted over the transducer 592. The additional matching layer component 595 can be configured with a peripheral portion P for sealing against the skin and any form of recesses 596 for capturing serum described above. In some treatments, the matching layer component 595 can have ridges or bumps with a sharper apex, as shown in FIGS. 9 and 14B for exfoliating a surface layer of skin. In some skin treatments, a single-use variation of an exfoliating tip may be used initially, followed by a non-exfoliating variation more adapted for serum penetration. In the variation of FIG. 18, the serum inflow channel 598 and the aspiration channel 599 are disposed in the transducer 592 as in the variation of FIGS. 17A-17B. In a similar variation, first and secondstacked single-use matching layer components (not shown) can be used to provide an assembly similar to that of FIGS. 15-16 wherein a gas flow is directed to a proximal porous or channeled matching layer, and serum is directed to a distal surface of the distal single-use matching layer.

In another variation, a feature of any of the applicators above comprises a contact sensor (not shown) in a distal tip of an applicator, which can provide a signal to the controller 175 when the distal tip contacts targeted skin thereby activating the ultrasound transducer only when in contact with targeted skin. A contact sensor can comprise a capacitance sensor, impedance sensor, or photonic sensor coupled to the controller 175. In another variation, the controller 175 can be connected to a pressure sensor in the negative pressure source 155 or in the aspiration channel that can sense pressure changes in the outflow channel of the system, which will indicate when the distal tip is sealed against the targeted skin. The controller 175 is then adapted to activate the ultrasound transducer only when the distal tip is in contact with targeted skin. In another variation, the applicator can carry a finger-actuated switch (not shown) for activating the ultrasound transducer.

In another variation, the distal tip of an applicator can carry an ultrasound transducer as described above, as well as at least one micro-actuator that produces subsonic vibrations or pressure waves. Such subsonic micro-actuators are disclosed in commonly invented U.S. Pat. No. 10,456,321. In use, the operator can have the option of actuating both the ultrasound transducer and the subsonic micro-actuator to enhance the permeabilization of tissue. The subsonic micro-actuators can be configured to deliver vibratory forces and pressure waves, either transverse or parallel, to the axis of the ultrasound transducer wave propagation. The combination of subsonic and ultrasonic forces on targeted skin can improve serum penetration.

In another variation, the systems described above can be further adapted to exfoliate skin by different mechanisms. First, in any variations above, the distal lip or periphery P around a transducer can carry sharp features such as diamond dust to abrade tissue. In a variation, the projecting spacing elements in the central portion of a distal tip may be sharp for exfoliation, as shown in FIG. 9B. In an alternative variation, the serum 115 can carry an abrasive powder such as diamond dust, ground walnut shells, or the like to abrade skin as the surface or periphery of the distal tip is moved over targeted tissue.

In another variation, a system as described above can be used to deliver a PRP (platelet-rich plasma) as a serum to targeted skin. While the invention has been described for delivery of serum to a subject's skin and lips for cosmetic and rejuvenation purposes, an applicator as described above can also be used for enhancing the delivery of any type of pharmaceuticals through an exfoliated skin surface, such as analgesics, anti-inflammatory drugs and the like.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications and patents cited herein are hereby incorporated by reference as if set forth in its entirety herein.

What is claimed is:

1. A method of enhancing permeability of a targeted skin comprising:

applying acoustic energy to a flow of a serum captured in a sealed space in a distal tip of an applicator, the applicator comprising a handle and an elongated shaft extending within the handle, wherein when the distal tip is against the targeted skin, the sealed space is defined by (i) an ultrasound transducer within the handle in a central portion of the distal tip, the ultrasound transducer comprising a lateral surface, the ultrasound transducer extending at a distal end of the elongated shaft, (ii) a peripheral sealing portion around a periphery of the distal tip configured to form a seal against the targeted skin, the distal tip comprising a recess defined by a wall of the distal tip, wherein the ultrasound transducer is received in the recess such that the lateral surface of the ultrasound transducer and an inner surface of the recess forms an annular space through which the serum is delivered from an interior chamber within the handle to the sealed space, wherein the interior chamber comprises an annular configuration around a central passageway through which the elongated shaft is received, and (iii) the targeted skin wherein applying acoustic energy from the ultrasound transducer causes a dimensional change in acoustically responsive media in the flow of the serum captured in the sealed space thereby creating acoustic pressure that loosens paracellular junctions in the targeted skin.

2. The method of claim 1 further comprising introducing the flow of the serum into the sealed space through at least one inflow port inward of the peripheral sealing portion.

3. The method of claim 2 including applying a negative pressure in the sealed space through an aspiration port inward of the peripheral sealing portion.

4. The method of claim 3 wherein the negative pressure causes the flow of serum into the sealed space from the at least one inflow port.

5. The method of claim 4 further comprising introducing a flow of gas into the distal tip to mix with the serum wherein the gas comprises the acoustically responsive media.

6. The method of claim 4 wherein the distal tip comprises a recessed region of the central portion that is recessed from the peripheral sealing portion.

7. The method of claim 6 wherein the recessed region is bounded by one or more spacing elements configured to space apart a surface of the ultrasound transducer and the targeted skin thereby maintaining a selected dimension of the sealed space for capturing serum.

8. The method of claim 7 wherein the one or more spacing elements comprise at least one of ridges, bumps and surfaces distal of the recessed region.

9. The method of claim 8 wherein the recessed region comprises at least one of channels, grooves, dimples, and bores.

10. The method of claim 7 wherein the surface of the ultrasound transducer comprises a matching layer disposed over a piezoelectric crystal and the one or more spacing elements and recessed region are carried in the matching layer.

11. The method of claim 10 wherein the acoustic energy is applied from the matching layer having a surface area of at least 1 cm2.

12. The method of claim 10 wherein the acoustic energy is applied from the matching layer having a surface area ranging from 1 cm2 to 20 cm2.

13. The method of claim 1 wherein the acoustic pressure has peak pressures of at least 0.1 MPa.

14. The method of claim 1 wherein applying acoustic energy is provided at a frequency range of 0.1 MHz to 10 MHz.

15. The method of claim 1 further including moving the distal tip over the targeted skin with the peripheral sealing portion forming a seal against the targeted skin to maintain the sealed space contemporaneous with introducing the serum.

16. A method of applying a serum to a targeted skin surface comprising providing a continuous flow of a serum and a continuous flow of a gas in an interface between an ultrasound transducer and targeted skin, the ultrasound transducer extending at a distal end of an elongated shaft within a handle, wherein the ultrasound transducer comprises a proximal matching layer and a distal matching layer, applying acoustic energy from the ultrasound transducer to the continuous flow of serum and gas in the interface and causing a dimensional change in gas mixed in the serum to thereby create an acoustic pressure that loosens paracellular junctions in the targeted skin to enhance penetration of the serum in the targeted skin, wherein the serum and the gas are mixed at a distal facing surface of the ultrasound transducer, wherein the distal facing surface is defined by the distal matching layer and comprises recesses that mixes the serum and the gas, wherein a distal tip of a handheld applicator and the continuous flow of serum flows between an inflow port and an outflow port in the distal tip, wherein the ultrasound transducer is received in a recess within the distal tip such that a lateral surface of the ultrasound transducer and an inner surface of the recess forms an annular space through which the serum is delivered to the targeted skin, wherein the serum is delivered from an interior chamber within the handle, the interior chamber comprising an annular configuration around a central passageway through which the elongated shaft is received.

17. The method of claim 16 wherein the interface comprises a sealed space for capturing the continuous flow of serum, wherein the sealed space is defined by (i) a matching layer of the ultrasound transducer, (ii) a peripheral sealing portion around a periphery of the ultrasound transducer configured to form a seal against the targeted skin, and (iii) the targeted skin.

18. The method of claim 16 wherein the continuous flow of serum between the inflow port and the outflow port is restricted by at least one flow restriction element between the inflow port and the outflow port in the distal tip.

* * * * *